United States Patent
Kim et al.

(10) Patent No.: US 7,526,959 B2
(45) Date of Patent: May 5, 2009

(54) METHOD OF INSPECTING A SUBSTRATE USING ULTRASONIC WAVES AND APPARATUS FOR PERFORMING THE SAME

(75) Inventors: Kwang-Soo Kim, Gyeonggi-do (KR); Chung-Sam Jun, Gyeonggi-do (KR)

(73) Assignee: Samsung Electronics Co., Ltd., Suwon-si, Gyeonggi-do (KR)

(*) Notice: Subject to any disclaimer, the term of this patent is extended or adjusted under 35 U.S.C. 154(b) by 0 days.

(21) Appl. No.: 11/428,804

(22) Filed: Jul. 5, 2006

(65) Prior Publication Data

US 2007/0022815 A1 Feb. 1, 2007

(30) Foreign Application Priority Data

Jul. 28, 2005 (KR) .................. 10-2005-0068710

(51) Int. Cl.
*G01N 29/04* (2006.01)
(52) U.S. Cl. .................. 73/628; 73/598; 73/600
(58) Field of Classification Search .......... 73/596–600, 73/602, 618, 620, 624, 625, 627, 628, 629, 73/632
See application file for complete search history.

(56) References Cited

U.S. PATENT DOCUMENTS

| | | | | |
|---|---|---|---|---|
| 4,523,468 A | * | 6/1985 | Derkacs et al. ............... | 73/598 |
| 4,603,584 A | * | 8/1986 | Bartle et al. .................. | 73/599 |
| 4,625,555 A | * | 12/1986 | Fujii ............................ | 73/597 |
| 4,630,226 A | * | 12/1986 | Tanaka ........................ | 702/103 |
| 4,741,212 A | * | 5/1988 | Rehwald ....................... | 73/600 |
| 4,866,614 A | * | 9/1989 | Tam ............................ | 600/437 |
| 5,113,697 A | * | 5/1992 | Schlawne .................... | 73/602 |
| 5,681,995 A | * | 10/1997 | Ooura et al. ................. | 73/622 |
| 6,467,352 B2 | * | 10/2002 | Schafer et al. ............... | 73/597 |
| 6,865,948 B1 | * | 3/2005 | Chen ........................... | 73/597 |
| 6,941,811 B2 | * | 9/2005 | Chen et al. ................... | 73/629 |

FOREIGN PATENT DOCUMENTS

| | | | |
|---|---|---|---|
| JP | 01-098961 | * | 4/1989 |
| JP | 2004-335570 | | 11/2004 |
| KR | 2002-0053621 | | 7/2002 |
| KR | 2004-0103045 | | 12/2004 |
| KR | 10-2005-0007482 | | 1/2005 |

OTHER PUBLICATIONS

English language abstract of Korean Publication No. 2002-0053621.
English language abstract of Korean Publication No. 2004-0103045.
English lanuage abstract of Japanese Publication No. 2004-335570.

* cited by examiner

*Primary Examiner*—Helen C. Kwok
(74) *Attorney, Agent, or Firm*—Marger Johnson & McCollom, P.C.

(57) ABSTRACT

A method of inspecting a substrate is provided comprising applying ultrasonic waves to a substrate, receiving echo pulse signals transmitted through the substrate, and analyzing received echo pulse signals to detect defects in the substrate. Thus, defects in the substrate may be detected.

27 Claims, 8 Drawing Sheets

410

METHOD OF INSPECTING A SUBSTRATE USING ULTRASONIC WAVES AND APPARATUS FOR PERFORMING THE SAME

CROSS REFERENCE TO RELATED APPLICATION

This application claims the benefit under 35 USC § 119 of Korean Patent Application No, 2005-68710 filed on Jul. 28, 2005 the disclosure of which is hereby incorporated herein by reference in its entirety as if set forth fully herein.

BACKGROUND OF THE INVENTION

1. Field of the Invention

The present invention relates to a method of inspecting a substrate and an apparatus for performing the same. More particularly, the present invention relates to a method of inspecting a substrate to detect defects in the substrate, such as a silicon wafer, and an apparatus for performing the same.

2. Description of the Related Art

A semiconductor device, in general, is manufactured by performing a fabrication process for forming electric circuits on a semiconductor substrate such as a silicon wafer, an electrical die sorting process for inspecting electric characteristics of the electric circuits formed on the semiconductor substrate, a packaging process for packaging semiconductor devices formed on the semiconductor substrate in epoxy resins and individuating the semiconductor devices.

The fabrication process includes a deposition process for forming a layer on the semiconductor substrate, a chemical mechanical polishing process for planarizing the layer, a photolithography process for forming a photoresist pattern on the layer, an etching process for forming the layer into patterns having electrical characteristics using the photoresist pattern, an ion implantation process for implanting ions into specific regions of the semiconductor substrate, a cleaning process for removing impurities from the semiconductor substrate, a drying process for drying the cleaned semiconductor substrate, an inspection process for inspecting defects of the layer or patterns, and the likes.

Semiconductor devices are manufactured by repeatedly performing the unit processes as described above, and semiconductor substrates are received in a container such as a cassette and a front opening unified pod (FOUP) and transferred between processing apparatuses for performing the unit processes. Further, each of the semiconductor substrates is transferred between the container and the processing apparatuses.

The semiconductor substrates are damaged while transferring the semiconductor substrates. For example, defects such as scratches at a surface of the semiconductor substrate, a chipping at an edge portion of the semiconductor substrate, etc., are frequently occurred. The defects are detected during the inspection process. For example, the defects occurred at the surface of the semiconductor substrate are detected by a dark field inspection apparatus using scattering of laser beam, a bright field inspection apparatus using a charge coupled device (CCD) image sensor, and the likes.

However, defects, such as cracks, occurred in the semiconductor substrate cannot be detected by the inspection apparatuses. The cracks in the semiconductor substrate may be propagated, thereby causing breakage of the semiconductor substrate. Further, due to the unexpected breakage of the semiconductor substrate, the manufacturing process of semiconductor device may be interrupted and the apparatuses may also be contaminated.

SUMMARY

Example embodiments of the present invention provide a method of inspecting a substrate capable of detecting interior defects of the substrate.

Example embodiments of the present invention also provide an apparatus for inspecting a substrate capable of detecting interior defects of the substrate.

In one aspect of the present invention, ultrasonic waves can be applied to a substrate, and echo pulse signals transmitted through the substrate can then received. Defects in the substrate may be detected by analyzing the echo pulse signals. In another embodiment, the ultrasonic waves can be applied to a central portion of the substrate. Preferably, the transmitted echo pulse signals can be received at a plurality of receiving locations on the substrate. More preferably, at least three receiving locations can be radially disposed around a center of the substrate. In a further embodiment, the receiving locations can be spaced at regular intervals.

In one embodiment, the ultrasonic waves can be obliquely applied with respect to the rear surface of the substrate and concentrically transmitted from the central portion to the edge portion of the substrate. In another embodiment, analyzing the received echo pulse signals includes processing the echo pulse signals to obtain detection data in connection with the defects, and comparing the detection data with reference data obtained from a reference substrate to detect the defects.

In one aspect of this invention, the ultrasonic waves can be transmitted from one of a plurality of transmitting/receiving locations disposed at regular intervals around a center of the substrate, and the echo pulse signals can be received at the remaining transmitting/receiving locations. In another aspect, the ultrasonic waves can be applied at an oblique angle of incidence to a central portion of the substrate, and the echo pulse signals reflected from the defects or a surface of the edge portion of the substrate can be received at the central portion of the substrate. Preferably, the subject method further comprises continuously applying the ultrasonic waves and continuously receiving the echo pulse signals while the substrate is moved in stepwise rotation. In a further aspect, the ultrasonic waves can be applied at oblique incidence angles to a central portion of the substrate and transmitted toward edge portions of the substrate, respectively, and the echo pulse signals reflected from the defects or the edge portions of the substrate can be received at the central portion of the substrate.

An apparatus for inspecting a substrate can be provided. The apparatus can comprise a stage for supporting a substrate, at least one ultrasonic transducer connected to the stage and in contact with a rear surface of the substrate for applying ultrasonic waves to the substrate and receiving echo pulse signals transmitted through the substrate, and an analyzer for analyzing the echo pulse signals received by the ultrasonic transducer to detect defects in the substrate. In one embodiment, a first ultrasonic transducer can be disposed at a central portion of the stage to apply the ultrasonic waves to a central portion of the substrate, and a plurality of second ultrasonic transducers can be disposed at a plurality of locations spaced from the central portion of the stage to receive the echo pulse signals. In another embodiment, the second ultrasonic transducers are spaced at regular intervals. In a further embodiment, a pulse generator can be connected to the first ultrasonic transducer for generating pulse signals, and a signal amplifier can be connected to the second ultrasonic transducers for amplifying the echo pulse signals received by the second ultrasonic transducers.

In one aspect herein, the analyzer can include an analog/digital converter for digitizing the amplified echo pulse signals, an operating unit for comparing detection data including the digitized echo pulse signals with reference data to detect the defects, and a data storage unit for storing the detection data and the reference data. Furthermore, it can comprise a display unit connected with the analyzer for displaying the detection data and the detected defects.

The ultrasonic transducer can include an ultrasonic oscillator for generating the ultrasonic waves, a transmitting layer for transmitting the ultrasonic waves emitted from a front surface of the ultrasonic oscillator to the substrate, and an absorbing layer for absorbing the ultrasonic waves emitted from a rear surface of the ultrasonic oscillator. The ultrasonic oscillator can have a disk shape and can emit the ultrasonic waves in a direction substantially perpendicular to the rear surface of the substrate. The ultrasonic oscillator preferably has a circular ring shape, and the front surface of the ultrasonic oscillator is obliquely disposed with respect to the rear surface of the substrate so that the ultrasonic waves are obliquely applied to the rear surface of the substrate.

The apparatus can include at least three ultrasonic transducers which can be disposed at locations spaced from a central portion of the substrate supported by the stage, the ultrasonic waves can be transmitted from one of the ultrasonic transducer, and the echo pulse signals can be received by the remaining ultrasonic transducers. Preferably, the ultrasonic transducer can be disposed to be in contact with a central portion of the substrate supported by the stage, to obliquely emit the ultrasonic waves with respect to the rear surface of the substrate and to receive the echo pulse signals reflected from the defects or a surface of the edge portion of the substrate. More preferably, the ultrasonic transducer can include an ultrasonic oscillator disposed to obliquely emit the ultrasonic waves with respect to the substrate, a transmitting layer for transmitting the ultrasonic waves emitted from a front surface of the ultrasonic oscillator to the substrate and an absorbing layer for absorbing the ultrasonic waves emitted from a rear surface of the ultrasonic oscillator. In another further embodiment, a rotational driving section can be provided for moving the ultrasonic oscillator in stepwise rotation.

In still a further embodiment, the ultrasonic transducer can be disposed to be in contact with a central portion of the substrate supported by the stage, to obliquely emit the ultrasonic waves to a central portion of the substrate so as to be transmitted to edge portions of the substrate, respectively, and to receive the echo pulse signals reflected from the defects or the edge portions of the substrate. Preferably, the ultrasonic transducer includes a plurality of ultrasonic oscillators disposed to obliquely emit the ultrasonic waves with respect to the substrate, a transmitting layer for transmitting the ultrasonic waves emitted from front surfaces of the ultrasonic oscillators to the substrate, and an absorbing layer for absorbing the ultrasonic waves emitted from rear surfaces of the ultrasonic oscillators.

In accordance with example embodiments of the present invention, the interior defects of the substrate may be detected by analyzing the echo pulse signals transmitted through the substrate, and in addition, unexpected breakage of the substrate may be prevented.

BRIEF DESCRIPTION OF THE DRAWINGS

Example embodiments of the present invention will become readily apparent along with the following detailed description when considered in conjunction with the accompanying drawings wherein.

DETAILED DESCRIPTION

Figure 1:
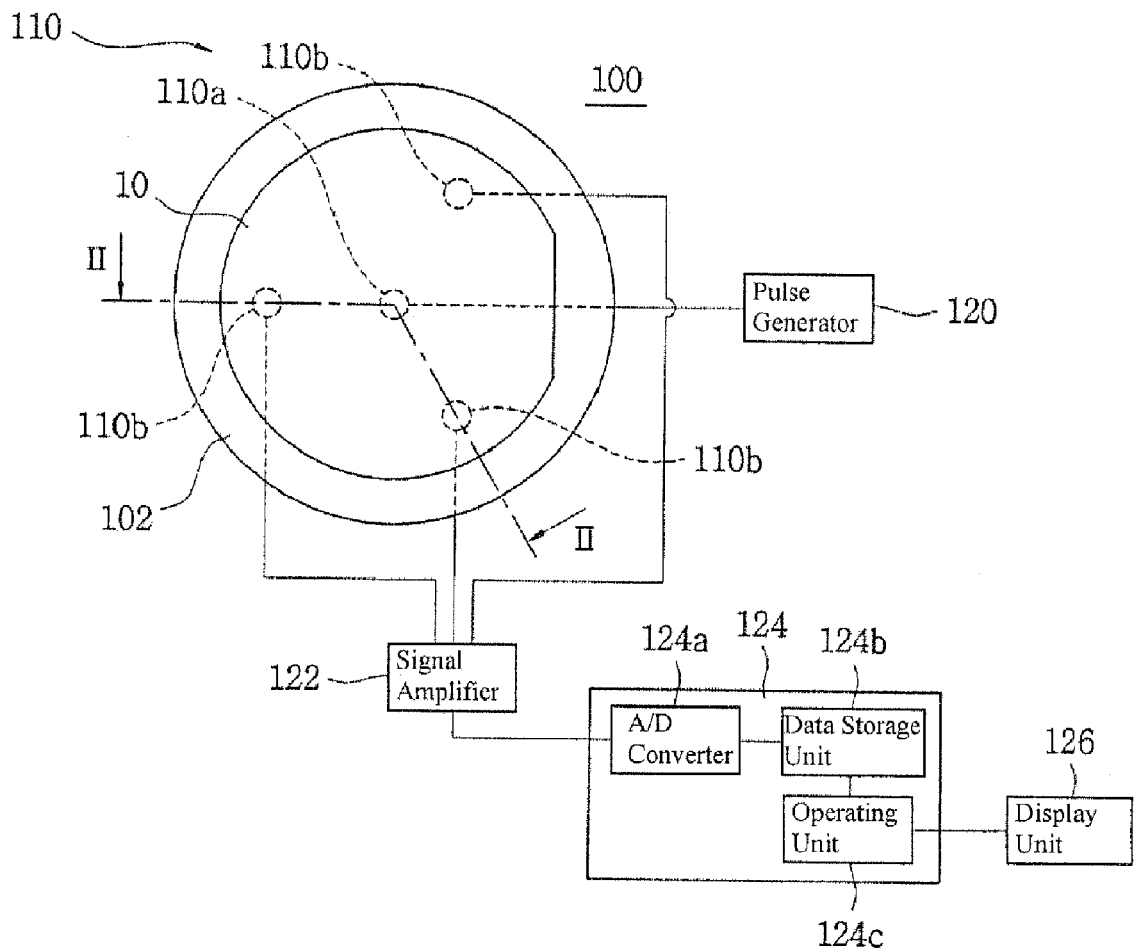
FIG. 1 is a schematic plan view illustrating an apparatus for inspecting a substrate in accordance with a first embodiment of the present invention.

Embodiments of the invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present. In contrast, when an element is referred to as being "directly on" another element, there are no intervening elements present. As used herein, the term "and/or" includes any and all combinations of one or more of the associated listed items.

It will be understood that, although the terms first, second, etc. may be used herein to describe various elements, these elements should not be limited by these terms. These terms are only used to distinguish one element from another. For example, a first thin film could be termed a second thin film, and, similarly, a second thin film could be termed a first thin film without departing from the teachings of the disclosure.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to other elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Embodiments of the present invention are described herein with reference to cross section illustrations that are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present invention.

Hereinafter, embodiments of the present invention will be explained in detail with reference to the accompanying drawings.

Figure 2:
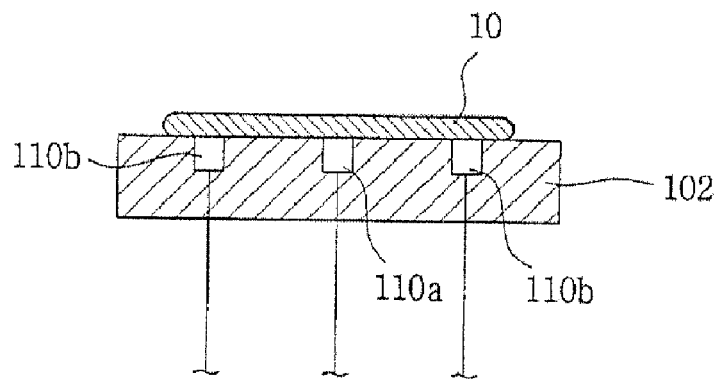
FIG. 2 is a cross-sectional view taken along a line II-II as shown in FIG. 1.

Referring to FIGS. 1 and 2, a substrate inspecting apparatus 100 in accordance with a first embodiment of the present invention may be employed for detecting defects in a semiconductor substrate 10, such as a silicon wafer.

The apparatus 100 may include a stage 102 for supporting the substrate 10. A plurality of ultrasonic transducers 110 may be built-in into the stage 102 to apply ultrasonic waves to the substrate 10 and to receive echo pulse signals transmitted through the substrate 10.

Particularly, a first ultrasonic transducer 110a serving as an ultrasonic emitter is disposed at a central portion of the stage to apply the ultrasonic waves to the substrate 10. A plurality of second ultrasonic transducer 110b serving as ultrasonic receivers is disposed around the first ultrasonic transducer 110a to receive the echo pulse signals transmitted through the substrate 10.

The first and second ultrasonic transducers 110a and 110b are built-in into the stage 102 to be in contact with a rear surface of the substrate 10 supported by the stage 102. At least three of the second ultrasonic transducers 110b are disposed at locations spaced from the first ultrasonic transducer 110a at regular intervals. Further, the second ultrasonic transducers 110b are spaced at regular intervals from each other. As shown in FIGS. 1 and 2, though three of the second ultrasonic transducers 110b are disposed around the first ultrasonic transducer 110a, however, the present invention is not limited by the number of the second ultrasonic transducers 110b described herein.

The first ultrasonic transducer 110a is connected with a pulse generator 120 for generating pulse signals of from about 0.5 to about 15 MHz. Each of the second ultrasonic transducers 110b is connected with a signal amplifier 122 for amplifying the echo pulse signals. The signal amplifier 122 is connected to an analyzer 124 for analyzing the amplified echo pulse signals to detect the interior defects of the substrate 10.

The analyzer 124 may include an analog/digital converter 124a (hereinafter "A/D converter") for digitizing the amplified echo pulse signals, a data storage unit 124b for storing detection data obtained from the amplified echo pulse signals and reference data used for ultrasonic signal analysis and an operating unit 124c for comparing the detection data with the reference data to detect the defects of the substrate 10. Further, the analyzer is connected with a display unit 126 for displaying the detected defects and the received echo pulse signals.

The stage 102 may be structured to hold the substrate 10 using electrostatic force or vacuum force.

Figure 3:
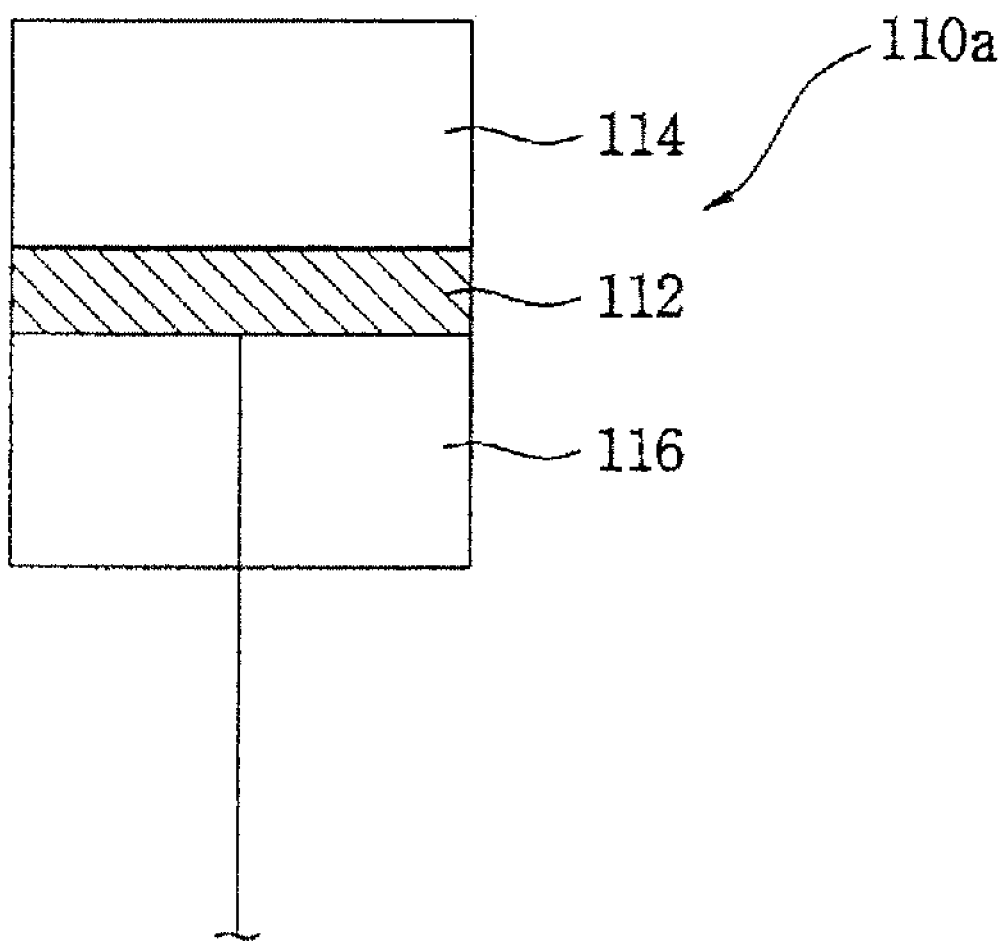
FIG. 3 is a cross-sectional view illustrating a first ultrasonic transducer as shown in FIG. 1.

Referring to FIG. 3, the first ultrasonic transducer 110a may include an ultrasonic oscillator 112, a transmitting layer 114 and an absorbing layer 116. The ultrasonic oscillator 112 has a disk shape and generates the ultrasonic waves based on the pulse signal. The transmitting layer 114 is provided to transmit the ultrasonic waves emitted from a front surface of the ultrasonic oscillator 112. The absorbing layer 116 is provided to absorb the ultrasonic waves emitted from a rear surface of the ultrasonic oscillator 112. Here, the ultrasonic oscillator 112 emits the ultrasonic waves in a direction substantially perpendicular to the rear surface of the substrate 10.

Each of the second ultrasonic transducers 110b may have substantially the same configuration as the first ultrasonic transducer 110a and may generate electrical signals corresponding to the echo pulse signals. The ultrasonic oscillator 112 may include a piezoelectric ceramic material such as PZT ($(PbZr)TiO_3$). The transmitting layer 114 may include epoxy resins or acrylic resins, and the absorbing layer 116 may include cork.

Figure 4:
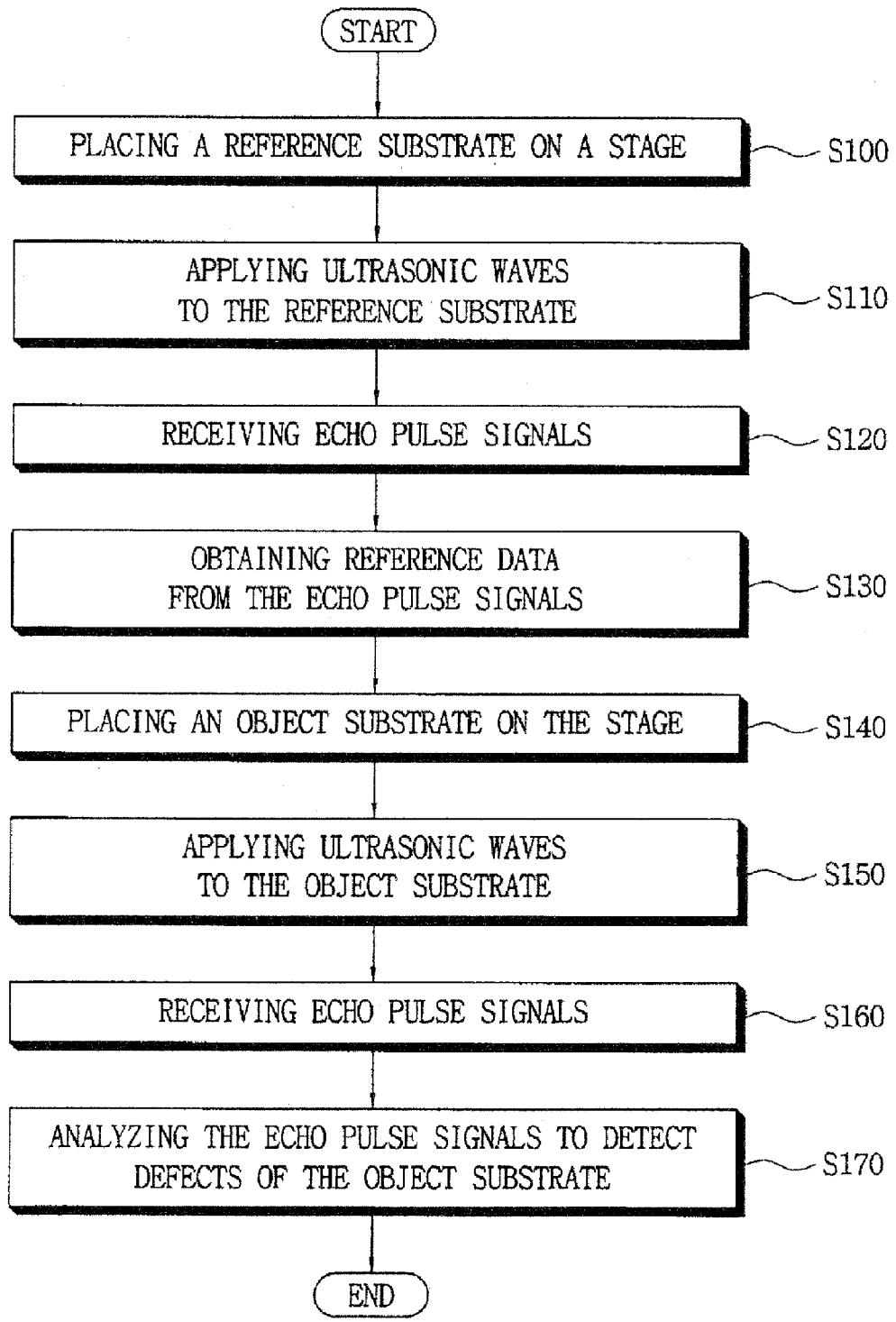
FIG. 4 is a flow chart illustrating a method of inspecting a substrate using the substrate inspecting apparatus as shown in FIG. 1.

Referring to FIG. 4, in step S100, a reference substrate without interior defects is placed on the stage 102.

In step S110, the ultrasonic waves are applied to the reference substrate by the first ultrasonic transducer 110a. Particularly, the pulse generator 120 generates a pulse signal and the ultrasonic oscillator 112 of the ultrasonic transducer 110a generates ultrasonic waves according to the pulse signal. The ultrasonic waves are applied to a central portion of the reference substrate placed on the stage 102.

In step S120, the echo pulse signals through the reference substrate are received. Particularly, the applied ultrasonic waves may be longitudinal waves and then converted into transverse waves in the reference substrate. The converted transverse waves are transmitted from the central portion of the reference substrate toward an edge portion of the reference substrate. Then, the converted transverse waves are reflected at a surface of the edge portion of the reference substrate. The second ultrasonic transducers receive the transmitted ultrasonic waves and the reflected echo pulse signals.

In step S130, reference data are obtained from the received echo pulse signals. In detail, the echo pulse signals received by the second ultrasonic transducers are amplified by the signal amplifier 122, and the amplified echo pulse signals are then converted into reference signal values by the A/D converter 124a. The reference data including the reference signal values are stored in the data storage unit 124b of the analyzer 124.

In step S140, an object substrate to be inspected is placed on the stage 102, after removing the reference substrate from the stage 102.

In step S150, the ultrasonic waves are applied to the object substrate by the first ultrasonic transducer 110a.

In step S160, the echo pulse signals transmitted through the object substrate are received by the second ultrasonic transducers 110b. The received echo pulse signals have data on interior defects of the object substrate.

In step S170, the interior defects of the object substrate are detected by analyzing the received echo pulse signals. Particularly, the received echo pulse signals are amplified by the signal amplifier 122 and then converted into detection signal values by the A/D converter 124a. The operating unit 124c of the analyzer 124 compares detection data including the detection signal values with the reference data to thereby detect the interior defects of the object substrate. The detection data and defect data, such as position, size, shape, and the like, may be displayed by the display unit 126. The detection data and the detect data are stored in the data storage unit 124b.

In accordance with the present embodiment, the interior defects of the object substrate, such as cracks occurred in the object substrate, may be readily detected. Further, surface defects of the object substrate may also be detected by adjusting the incidence angle of the applied ultrasonic waves.

Figure 5:
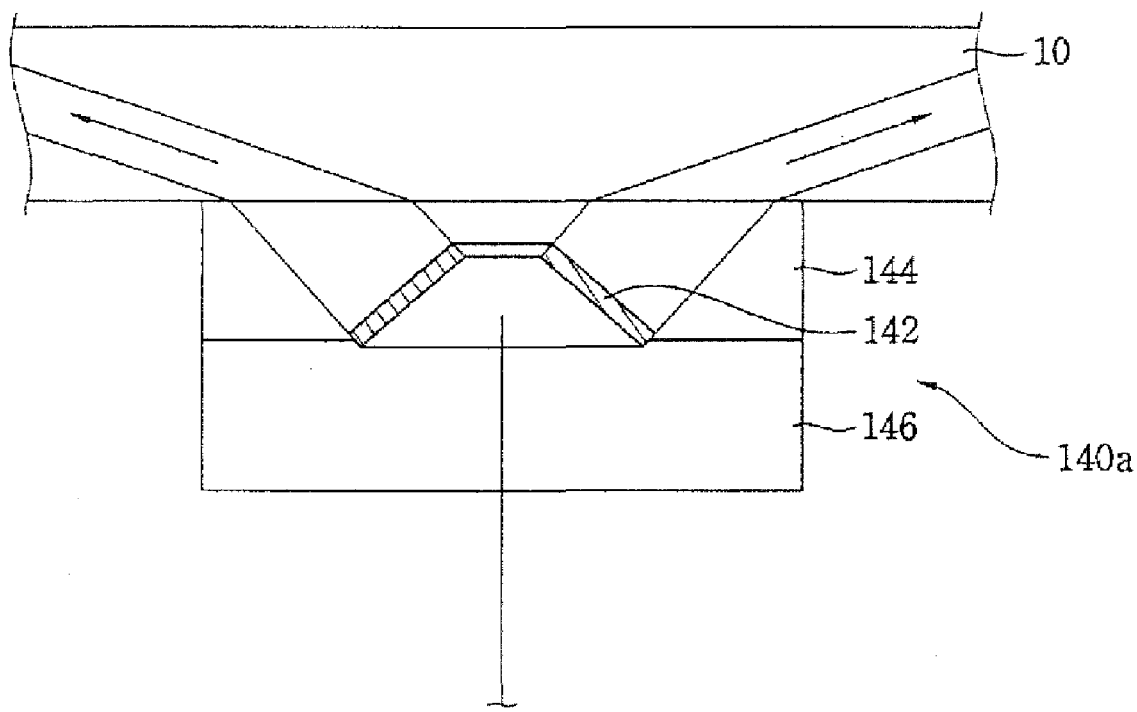
FIG. 5 is a cross-sectional view illustrating another example of the first ultrasonic transducer as shown in FIG. 1.
Figure 6:
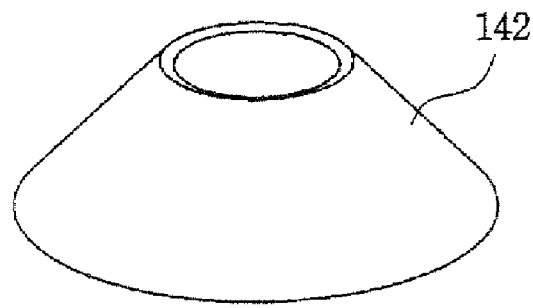
FIG. 6 is a perspective view illustrating an ultrasonic oscillator as shown in FIG. 5.

Referring to FIGS. 5 and 6, a first ultrasonic transducer 140a may include an ultrasonic oscillator 142 for generating ultrasonic waves, a transmitting layer 144 for transmitting the ultrasonic waves emitted from a front surface of the ultrasonic oscillator 142 to the substrate 10, and an absorbing layer 146 for absorbing the ultrasonic waves emitted from a rear surface of the ultrasonic oscillator 142. The ultrasonic oscillator 142 has a circular ring shape, and the front surface of the ultrasonic oscillator 142 is obliquely disposed with respect to the rear surface of the substrate 10 so that the ultrasonic waves may be obliquely applied to the rear surface of the substrate 10 and then transmitted to the edge portion of the substrate 10. The ultrasonic oscillator 142 may include a piezoelectric material such as PZT ($(PbZr)TiO_3$). The transmitting layer 144 may include epoxy resins or acrylic resins, and the absorbing layer 146 may include cork.

The ultrasonic waves emitted obliquely with respect to the rear surface of the substrate 10 may be converted into transverse waves and then transmitted concentrically from the central portion toward the edge portion of the substrate 10. The incidence angle of the ultrasonic waves may be variably adjusted, in one embodiment equal to or more than about 45°, in another embodiment equal to or more than about 60°, and in a further embodiment equal to or more than about 70°.

Alternatively, the incidence angle of the ultrasonic waves can become lower than or equal to about 39°. In such case, the ultrasonic waves may be converted into surface waves at a surface portion of the substrate 10. The converted surface waves may be transmitted along the surface portion of the substrate 10, and thus the surface defects of the substrate 10 may be detected.

The second ultrasonic transducers may have a substantially same configuration as the first ultrasonic transducer 140a.

Figure 7:
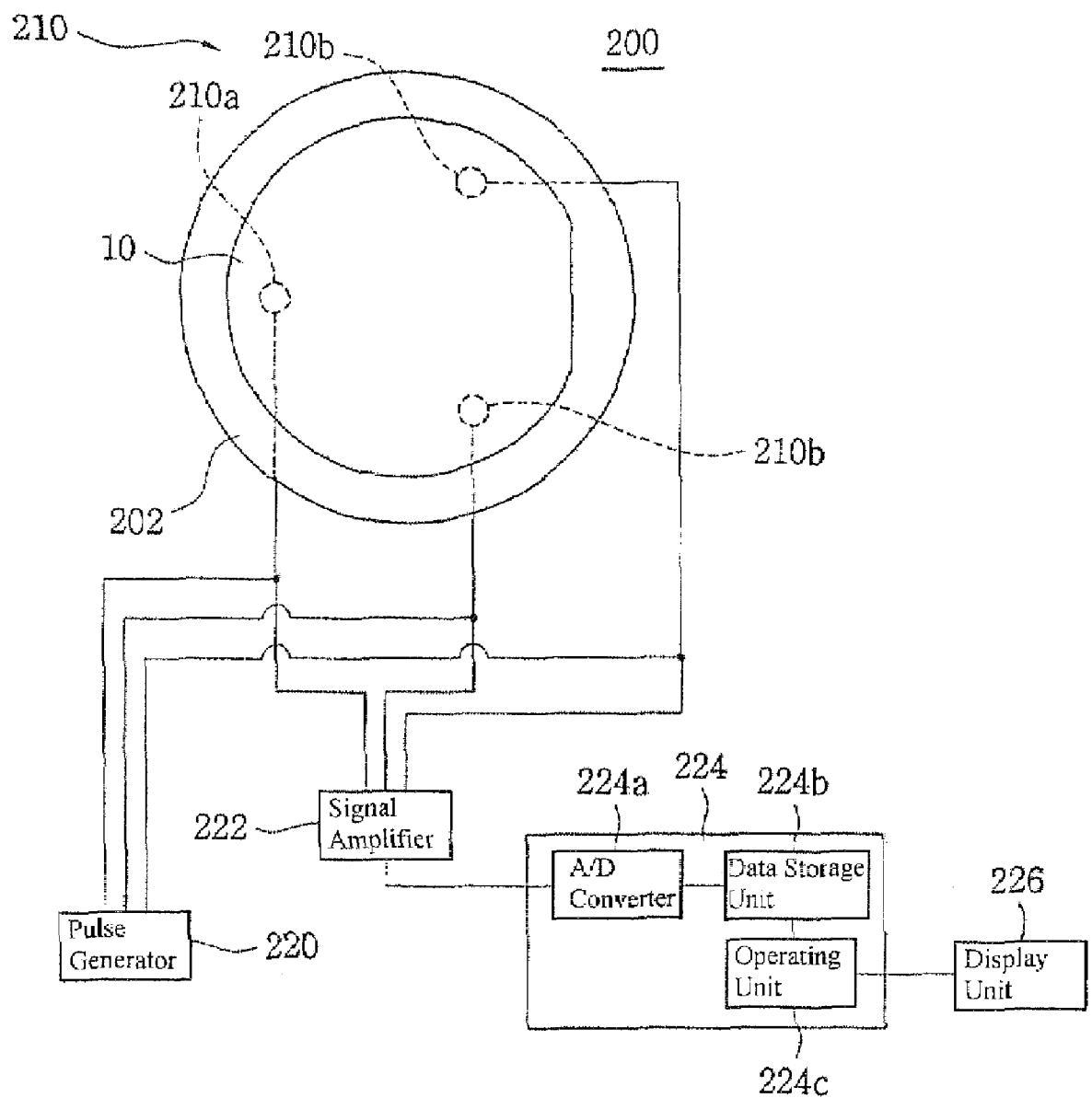
FIG. 7 is a schematic plan view illustrating an apparatus for inspecting a substrate in accordance with a second embodiment of the present invention.

Referring to FIG. 7, a substrate inspecting apparatus 200 may include a stage 202 for supporting a semiconductor substrate such as a silicon wafer and a plurality of ultrasonic transducers 210 for applying ultrasonic waves to the substrate 10 or receiving echo pulse signals transmitted through the substrate 10.

The ultrasonic transducers 210 are connected with a pulse generator 220 and a signal amplifier 222. The signal amplifier 222 is connected with an analyzer 224. The analyzer 224 may include an A/D converter 224a for converting the echo pulse signals into digital signal values, a data storage unit 224b for storing detection data and reference data, and an operating unit 224c for comparing the detection data with the reference data to detect interior defects of the substrate 10. Further, the analyzer 224 is connected with a display unit 226 for displaying the defects detected by the analyzer 224.

The ultrasonic transducers 210 are disposed at transmitting/receiving locations spaced at regular intervals from a center of the substrate 10 supported by the stage 202. Particularly, at least three ultrasonic transducers 210 are disposed at the transmitting/receiving locations spaced at regular intervals from the center of the substrate 10. Further, the transmitting/receiving locations are spaced at regular intervals from each other.

The pulse generator 220 provides pulse signals to one 210a of the ultrasonic transducers 210, and the ultrasonic transducer 210a generates the ultrasonic waves based on the pulse signals. The ultrasonic waves are emitted, typically perpendicularly or obliquely with respect to the substrate 10, and are transmitted through the substrate 10.

The remaining ultrasonic transducers 210b receive the echo pulse signals transmitted through the substrate 10, and the received echo pulse signals are provided to the analyzer 224 via the signal amplifier 222. The operating unit 224c compares the detection data including the signal values converted by the A/D converter 224a with the reference data stored in the data storage unit 224b, thereby detecting the interior defects of the substrate 10. The detected defects are displayed by the display unit 226.

As shown in the aforementioned FIGS., though three ultrasonic transducers 210 are employed in the substrate inspecting apparatus 200, the present invention is not be limited by the number of the ultrasonic transducers 210.

A method of inspecting the defects using the apparatus 200 in accordance with the present embodiment is substantially similar to that already described in connection with the steps as shown in FIG. 4. That is, reference data may be obtained from a reference substrate, and interior defects of an object substrate to be inspected may be detected by comparing detection data obtained from the object substrate with the reference data.

Figure 8:
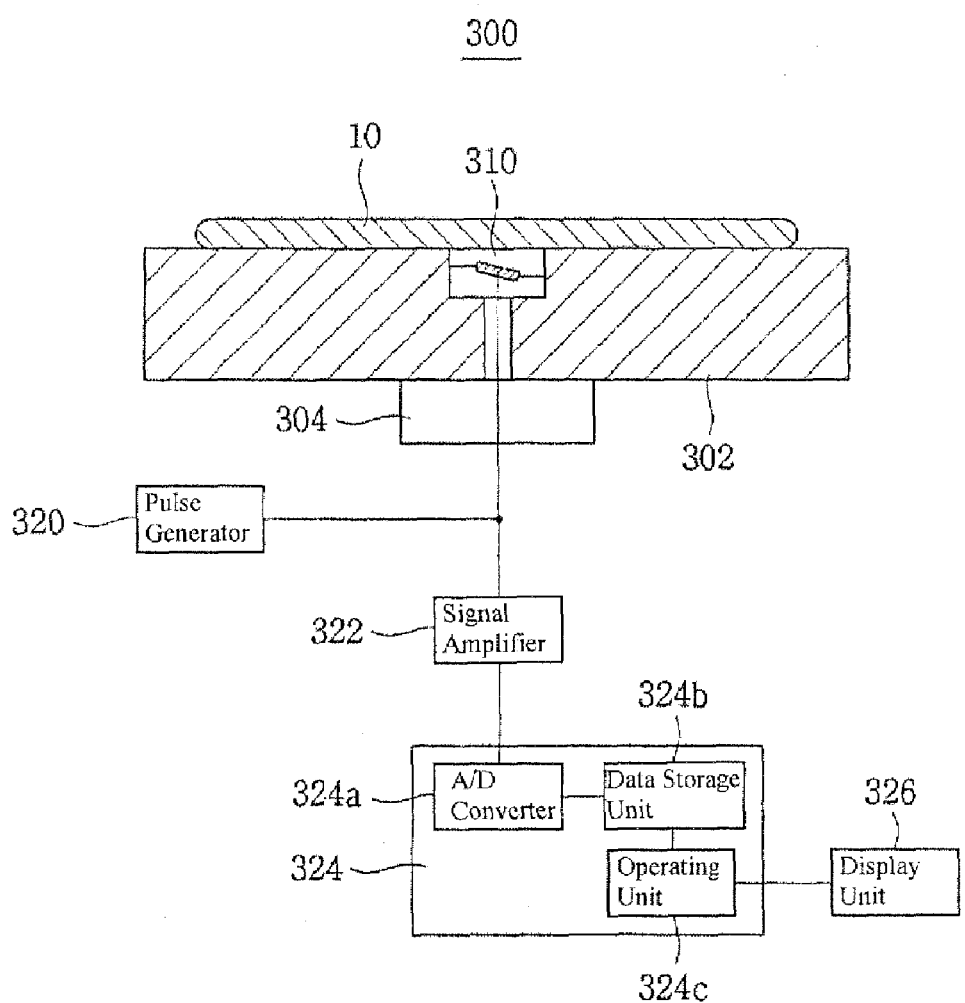
FIG. 8 is a schematic plan view illustrating an apparatus for inspecting a substrate in accordance with a third embodiment of the present invention.
Figure 9:
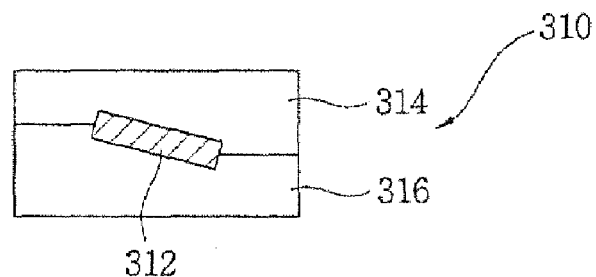
FIG. 9 is a cross-sectional view illustrating an ultrasonic transducer as shown in FIG. 8.

Referring to FIGS. 8 and 9, a substrate inspecting apparatus 300 in accordance with the third embodiment of the present invention may include a stage 302 for supporting a semiconductor substrate 10 and an ultrasonic transducer 310 for applying ultrasonic waves to the substrate 10 and receiving echo pulse signals transmitted through the substrate 10.

The ultrasonic transducer 310 may be built-in into the stage 302 to be in contact with a rear surface of the substrate 10 supported by the stage 302 and connected with a pulse generator 320 for generating pulse signals and a signal amplifier 322 for amplifying the received echo pulse signals. Further, the signal amplifier 322 is connected with an analyzer 324 for analyzing the received echo pulse signals to detect interior defects of the substrate 10. The analyzer 324 is connected with a display unit 326 for displaying the received echo pulse signals and the detected defects.

The analyzer 324 may include an A/D converter 324a for converting the received echo pulse signals into digital signal values, a data storage unit 324b for reference data and detection data and an operating unit 324c for comparing the detection data with the reference data to detect the interior defects of the substrate 10.

The ultrasonic transducer 310 may include an ultrasonic oscillator 312 for generating the ultrasonic waves according to the pulse signals, a transmitting layer 314 for transmitting the ultrasonic waves emitted from a front surface of the ultrasonic oscillator 312 to the substrate 10, and an absorbing layer 316 for absorbing the ultrasonic waves emitted from a rear surface of the oscillator 312.

The ultrasonic oscillator 312 is obliquely disposed with respect to the substrate 10 so that the ultrasonic waves have an oblique angle of incidence. The ultrasonic waves may be longitudinal waves which are converted into transverse waves after being applied into the substrate 10. Then, the converted ultrasonic waves are transmitted through the substrate 10 and reflected from the interior defects or a surface of an edge portion of the substrate 10. The reflected ultrasonic waves (or echo pulse signals) are received by the ultrasonic transducer 310. Here, the incidence angle of the ultrasonic waves may be variably adjusted, in one embodiment equal to or more than about 45°, in another embodiment equal to or more than about 60°, and in a further embodiment equal to or more than about 70°.

Alternatively, the incidence angle of the ultrasonic waves can become lower than or equal to about 39°. In such case, the ultrasonic waves may be converted into surface waves at a surface portion of the substrate 10. The converted surface waves may be transmitted along the surface portion of the substrate 10, and thus surface defects of the substrate 10 may be detected by analyzing echo pulse signals reflected from the surface defects.

The ultrasonic transducer 310 is connected with a rotational driving section 304 through the stage 302. The rotational driving section 304 rotates the ultrasonic transducer 310 in a stepwise manner so that an inspection process using the substrate inspecting apparatus 300 may be performed on the entire substrate 10.

Figure 10:
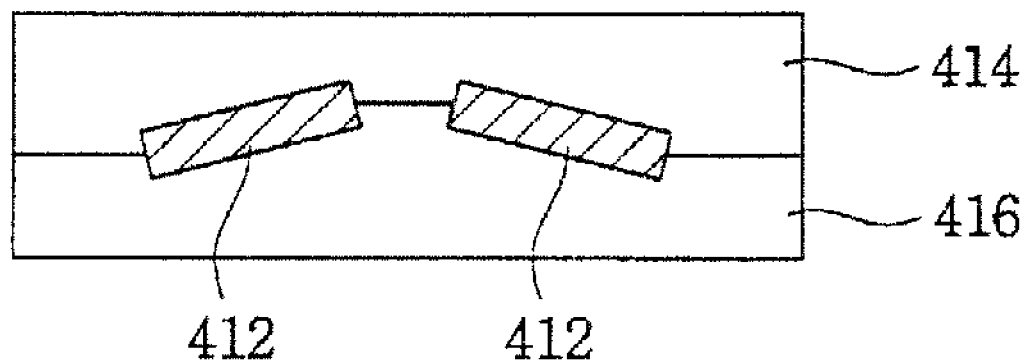
FIG. 10 is a cross-sectional view illustrating another example of the ultrasonic transducer as shown in FIG. 8.

Referring to FIG. 10, an ultrasonic transducer 410 may include a pair of ultrasonic oscillators 412 for emitting ultrasonic waves in directions opposite to each other, respectively, a transmitting layer 414 for transmitting the ultrasonic waves emitted from front surfaces of the ultrasonic oscillators 412 to the substrate 10 and an absorbing layer 416 for absorbing the ultrasonic waves emitted from rear surfaces of the ultrasonic oscillators 412.

When the ultrasonic transducer 410 including the pair of ultrasonic oscillators 412 is used in an inspection process, the time required for inspecting the substrate 10 may be reduced. Alternatively, the number of the ultrasonic oscillators 412 may be increased to reduce the time required for the inspection process. That is, a plurality of ultrasonic transducers may be radially disposed around a center of the substrate 10 supported by the stage 302. Ultrasonic waves are obliquely emitted to the rear surface of the substrate 10, respectively, and transmitted from a central portion toward edge portions of the substrate 10.

Figure 11:
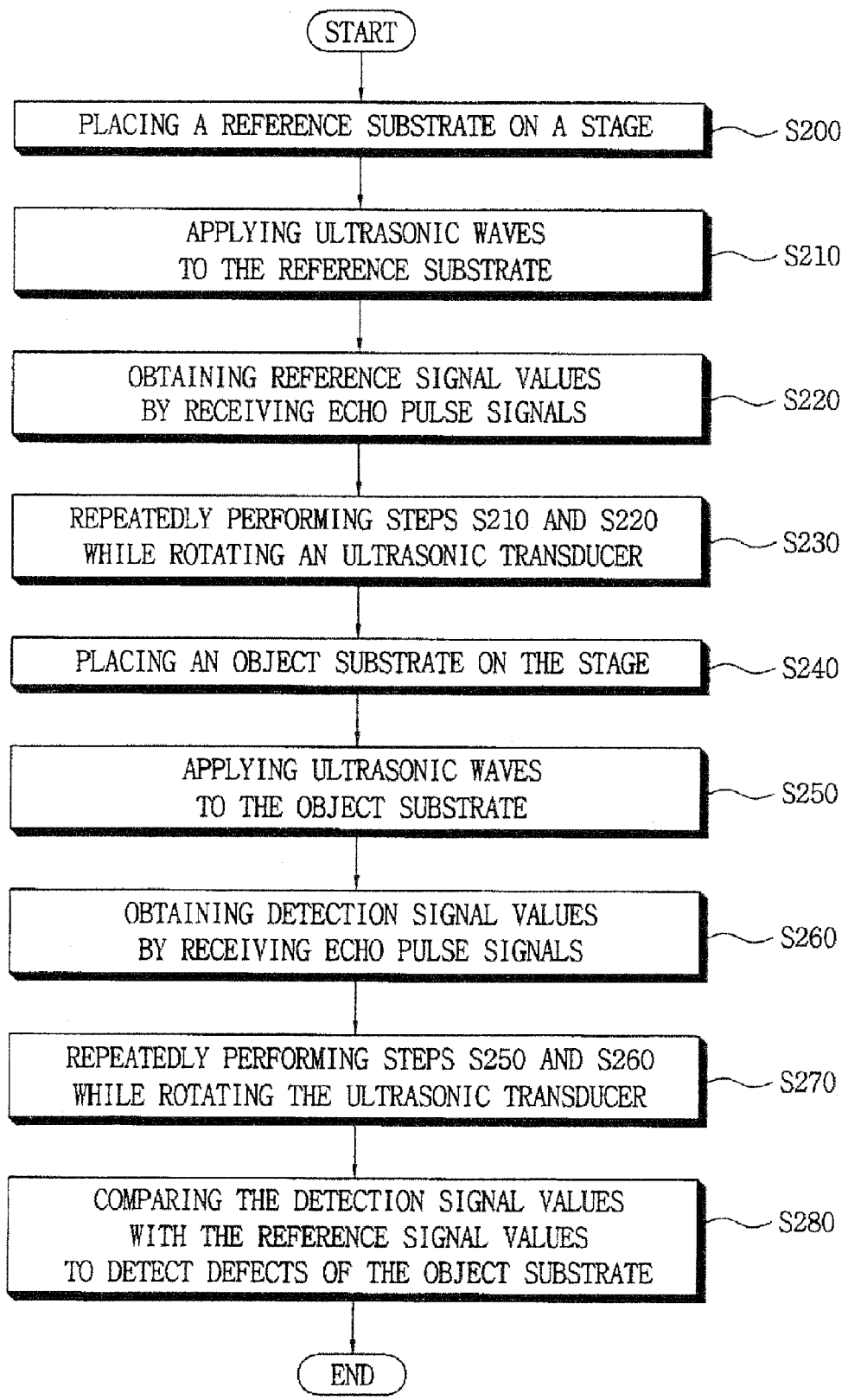
FIG. 11 is a flow chart illustrating a method of inspecting a substrate using the substrate inspecting apparatus as shown in FIG. 8.

Referring to FIG. 11, in step S200, a reference substrate without defects is placed on the stage 302.

In step S210, ultrasonic waves are obliquely applied to a central portion of the reference substrate. An incidence angle of the ultrasonic waves may be determined by an inclined angle of the ultrasonic oscillator 312 with respect to a rear surface of the reference substrate, and the ultrasonic waves may be converted into transverse waves transmitted through the reference substrate or surface waves transmitted along a surface of the reference substrate in accordance with the incidence angle thereof. The converted ultrasonic waves are transmitted toward an edge portion of the reference substrate and reflected from a surface of the edge portion of the reference substrate.

In step S220, reference signal values are obtained from echo pulse signals. The echo pulse signals reflected from the surface of the edge portion of the reference substrate are received by the ultrasonic transducer 310. The received echo pulse signals are amplified by the signal amplifier 322 and digitized into the reference signal values by the A/D converter 324a. Reference signal values are stored in the data storage unit 423b.

In step S230, the steps S210 and S220 are repeatedly performed while the ultrasonic transducer 310 is rotated in the stepwise manner, thereby obtaining reference signal values are obtained from the reference substrate. Reference data including the obtained reference signal values are stored in the data storage unit 324b.

In step S240, an object substrate to be inspected is placed on the stage 302 after removing the reference substrate from the stage 302.

In step S250, ultrasonic waves are obliquely applied to a central portion of the object substrate.

In step S260, echo pulse signals reflected from defects of the object substrate or a surface of an edge portion of the object substrate are received, and detection signal values are obtained from the received echo pulse signals.

In step S270, the steps S250 and S260 are repeatedly performed while the ultrasonic transducer 310 is rotated in the stepwise manner, thereby obtaining detection signal values from the object substrate.

In step S280, the defects of the object substrate are detected by comparing detection data including the detection signal values with the reference data using the operating unit 324c. The detected defects are stored in the data storage unit 324b and displayed by the display unit 326 along with the detection data.

In accordance with the example embodiments of the present invention, the interior defects, such as cracks, occurred in the substrate may be detected without difficulty by applying the ultrasonic waves to the substrate and then receiving the echo pulse signals transmitted through the substrate. Further, the surface defects of the substrate may also be detected by adjusting the incidence angle of the ultrasonic waves. Thus, unexpected breakage of the semiconductor substrate may be prevented.

Moreover, semiconductor manufacturing processes may be prevented from being interrupted because of the unexpected breakage of the semiconductor substrate, and contamination of semiconductor manufacturing apparatuses may also be prevented.

Although the example embodiments of the present invention have been described, it is understood that the present invention should not be limited to these example embodiments but various changes and modifications can be made by one skilled in the art within the spirit and scope of the present invention as hereinafter claimed.

What is claimed is:

1. A method of inspecting a semiconductor substrate comprising:
    applying ultrasonic waves to a central portion of a substantially flat surface of the semiconductor substrate to produce echo pulse signals as the ultrasonic waves interact with the semiconductor substrate;
    receiving the echo pulse signals transmitted through the semiconductor substrate at a plurality of receiving locations in contact with the surface of the semiconductor substrate; and
    analyzing the received echo pulse signals to detect defects in the semiconductor substrate, wherein the ultrasonic waves are concentrically transmitted from the central portion to an edge portion of the semiconductor substrate.

2. The method of claim 1, wherein at least three receiving locations are radially disposed around a center of the semiconductor substrate.

3. The method of claim 2, wherein the receiving locations are spaced at regular intervals in a stage supporting the semiconductor substrate.

4. The method of claim 1, wherein the ultrasonic waves are obliquely applied with respect to a rear surface of the semiconductor substrate.

5. The method of claim 1, wherein analyzing the received echo pulse signals includes:
    processing the echo pulse signals to obtain detection data in connection with the defects; and
    comparing the detection data with reference data obtained from a reference substrate to detect the defects.

6. The method of claim 1, wherein the ultrasonic waves are transmitted from one of a plurality of transmitting/receiving locations disposed at regular intervals around a center of the semiconductor substrate in a stage supporting the semiconductor substrate, and the echo pulse signals are received at the remaining transmitting/receiving locations disposed in the stage.

7. The method of claim 1, wherein the ultrasonic waves are applied at an oblique angle of incidence to the central portion of the semiconductor substrate, and the echo pulse signals reflected from the defects or a surface of an edge portion of the semiconductor substrate are received at the central portion of the semiconductor substrate.

8. The method of claim 7, further comprising continuously applying the ultrasonic waves and continuously receiving the echo pulse signals while the semiconductor substrate is moved in stepwise rotation about an axis normal to the central portion of the semiconductor substrate.

9. The method of claim 1, wherein the ultrasonic waves are applied at oblique incidence angles to the central portion of the semiconductor substrate and transmitted toward edge portions of the semiconductor substrate, respectively, and the echo pulse signals reflected from the defects or the edge portions of the semiconductor substrate are received at the central portion of the semiconductor substrate.

10. An apparatus for inspecting a substrate comprising:
    a stage for supporting a substrate, wherein the stage is in contact with a substantially entire rear surface of the substrate;
    at least one ultrasonic transducer disposed in the stage and in contact with a rear surface of the substrate for applying ultrasonic waves to the substrate and receiving echo pulse signals transmitted through the substrate; and
    an analyzer for analyzing the echo pulse signals received by the ultrasonic transducer to detect defects in the substrate, wherein a first ultrasonic transducer is disposed at a central portion of the stage to apply the ultrasonic waves to a central portion of the rear surface of the substrate, and a plurality of second ultrasonic transducers are disposed at a plurality of locations spaced from the central portion of the stage to receive the echo pulse signals.

11. The apparatus of claim 10, wherein the second ultrasonic transducers are spaced at regular intervals.

12. The apparatus of claim 10, further comprising a pulse generator connected to the first ultrasonic transducer for generating pulse signals and a signal amplifier connected to the second ultrasonic transducers for amplifying the echo pulse signals received by the second ultrasonic transducers.

13. The apparatus of claim 12, wherein the analyzer includes an analog/digital converter for digitizing the amplified echo pulse signals, an operating unit for comparing detection data including the digitized echo pulse signals with reference data to detect the defects, and a data storage unit for storing the detection data and the reference data.

14. The apparatus of claim 13, further comprising a display unit connected with the analyzer for displaying the detection data and the detected defects.

15. The apparatus of claim 10, wherein the ultrasonic transducer includes an ultrasonic oscillator for generating the ultrasonic waves, a transmitting layer for transmitting the ultrasonic waves emitted from a front surface of the ultrasonic oscillator to the substrate, and an absorbing layer for absorbing the ultrasonic waves emitted from a rear surface of the ultrasonic oscillator.

16. The apparatus of claim 15, wherein the ultrasonic oscillator has a disk shape and emits the ultrasonic waves in a direction substantially perpendicular to the rear surface of the substrate.

17. The apparatus of claim 15, wherein the ultrasonic oscillator has a circular ring shape, and the front surface of the ultrasonic oscillator is obliquely disposed with respect to the rear surface of the substrate so that the ultrasonic waves are obliquely applied to the rear surface of the substrate.

18. An apparatus for inspecting a substrate comprising:
    a stage for supporting a substrate, wherein the stage is in contact with a substantially entire rear surface of the substrate;
    at least one ultrasonic transducer disposed in the stage and in contact with a rear surface of the substrate for applying ultrasonic waves to the substrate and receiving echo pulse signals transmitted through the substrate; and
    an analyzer for analyzing the echo pulse signals received by the ultrasonic transducer to detect defects in the substrate, wherein the ultrasonic transducer is disposed to be in contact with a central portion of the substrate supported by the stage, to obliquely emit the ultrasonic waves with respect to the rear surface of the substrate and to receive the echo pulse signals reflected from the defects or a surface of an edge portion of the substrate.

19. The apparatus of claim 18, wherein the ultrasonic transducer includes an ultrasonic oscillator disposed to obliquely emit the ultrasonic waves with respect to the substrate, a transmitting layer for transmitting the ultrasonic waves emitted from a front surface of the ultrasonic oscillator to the substrate and an absorbing layer for absorbing the ultrasonic waves emitted from a rear surface of the ultrasonic oscillator.

20. The apparatus of claim 19, further comprising a rotational driving section for moving the ultrasonic oscillator in stepwise rotation.

21. The apparatus of claim 10, wherein the ultrasonic transducer is disposed to be in contact with a central portion of the substrate supported by the stage, to obliquely emit the ultrasonic waves to a central portion of the substrate so as to be transmitted to edge portions of the substrate, respectively, and to receive the echo pulse signals reflected from the defects or the edge portions of the substrate.

22. The apparatus of claim 21, wherein the ultrasonic transducer includes a plurality of ultrasonic oscillators disposed to obliquely emit the ultrasonic waves with respect to the substrate, a transmitting layer for transmitting the ultrasonic waves emitted from front surfaces of the ultrasonic oscillators to the substrate, and an absorbing layer for absorbing the ultrasonic waves emitted from rear surfaces of the ultrasonic oscillators.

23. A method of inspecting a semiconductor substrate comprising:

placing the semiconductor substrate on a stage such that a substantially flat rear surface of the semiconductor substrate contacts a substantially flat surface of the stage, the stage comprising at least one ultrasonic transmitter disposed at a central portion of the stage and a plurality of ultrasonic receivers disposed around the ultrasonic transmitter at regular intervals from each other;

applying ultrasonic waves to the rear surface of the semiconductor substrate from the ultrasonic transmitter;

receiving echo pulse signals from the rear surface of the semiconductor substrate at the ultrasonic receiver;

amplifying the received echo pulse signals;

digitizing the amplified echo pulse signals to obtain detection data in connection with defects in the semiconductor substrate;

comparing the detection data with reference data obtained from a reference substrate to detect the defects;

displaying the detected defects; and storing the detection data.

24. The method of claim 23, further comprising obtaining the reference data, including:

placing a reference substrate on the stage;

applying ultrasonic waves to the reference substrate;

obtaining the reference data by receiving echo pulse signals transmitted through the reference substrate; and storing the reference data.

25. The method of claim 23, wherein placing the semiconductor substrate on the stage includes applying one of a vacuum force and an electrostatic force to hold the semiconductor substrate on the stage.

26. The method of claim 1, wherein the echo pulse signals are reflected from interior defects or a surface of an edge portion of the semiconductor substrate.

27. The method of claim 10, wherein the echo pulse signals are reflected from interior defects or a surface of an edge portion of the semiconductor substrate.

* * * * *

UNITED STATES PATENT AND TRADEMARK OFFICE
CERTIFICATE OF CORRECTION

PATENT NO. : 7,526,959 B2
APPLICATION NO. : 11/428804
DATED : May 5, 2009
INVENTOR(S) : Kwang-Soo Kim et al.

It is certified that error appears in the above-identified patent and that said Letters Patent is hereby corrected as shown below:

Column 7, line 25, the word "detect" should read --defect--.

Signed and Sealed this

Twenty-third Day of November, 2010

David J. Kappos
*Director of the United States Patent and Trademark Office*